United States Patent
Bischoff et al.

(10) Patent No.: US 10,251,785 B2
(45) Date of Patent: Apr. 9, 2019

(54) METHOD FOR EYE SURGERY

(71) Applicant: Carl Zeiss Meditec AG, Jena (DE)

(72) Inventors: Mark Bischoff, Jena (DE); Gregor Stobrawa, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 996 days.

(21) Appl. No.: 14/027,272

(22) Filed: Sep. 16, 2013

(65) Prior Publication Data

US 2014/0081249 A1 Mar. 20, 2014

Related U.S. Application Data

(60) Provisional application No. 61/701,356, filed on Sep. 14, 2012.

(30) Foreign Application Priority Data

Sep. 14, 2012 (DE) .................. 10 2012 018 420

(51) Int. Cl.
*A61F 9/008* (2006.01)
*A61F 9/009* (2006.01)

(52) U.S. Cl.
CPC .......... *A61F 9/00804* (2013.01); *A61F 9/009* (2013.01); *A61F 9/00827* (2013.01); *A61F 9/00831* (2013.01); *A61F 9/00834* (2013.01); *A61F 9/00836* (2013.01); *A61F 2009/00872* (2013.01); *A61F 2009/00897* (2013.01)

(58) Field of Classification Search
CPC .............. A61F 9/00804; A61F 9/00827; A61F 9/00831; A61F 9/00834; A61F 9/00836; A61F 9/009; A61F 2009/00872; A61F 2009/00897; A61F 9/08036
USPC ............................................................ 606/5
See application file for complete search history.

(56) References Cited

U.S. PATENT DOCUMENTS

| | | | |
|---|---|---|---|
| 5,656,186 A | 8/1997 | Mourou et al. | |
| 8,388,608 B1 * | 3/2013 | Kaluzna | A61F 9/00831 606/4 |
| 2006/0235513 A1 * | 10/2006 | Price, Jr. | A61F 2/147 623/5.12 |
| 2007/0282313 A1 * | 12/2007 | Huang | A61B 3/1005 606/5 |

(Continued)

FOREIGN PATENT DOCUMENTS

| | | |
|---|---|---|
| DE | 69500997 T2 | 4/1998 |
| DE | 102005040338 A1 | 3/2007 |

(Continued)

*Primary Examiner* — Gary Jackson
*Assistant Examiner* — Zahed Kabir
(74) *Attorney, Agent, or Firm* — Leydig, Voit & Mayer, Ltd.

(57) ABSTRACT

A planning unit produces control data for a treatment device for eye surgery which produces at least one cutting surface in a cornea of the eye using a laser unit. The planning unit includes a calculation module for establishing a cornea cutting surface. The calculation module is configured to establish the cornea cutting surface based on data of a refraction correction, to produce a control data set for actuating the laser unit for the cornea cutting surface, and to determine the cornea cutting surface in such a way that the cornea cutting surface contributes to fixing an implant in an interlocking manner.

13 Claims, 4 Drawing Sheets

(56) References Cited

U.S. PATENT DOCUMENTS

| | | | |
|---|---|---|---|
| 2008/0183159 A1 | 7/2008 | Preuss et al. | |
| 2008/0275433 A1 | 11/2008 | Russmann et al. | |
| 2008/0319428 A1* | 12/2008 | Wiechmann | A61F 9/008 606/5 |
| 2010/0087802 A1* | 4/2010 | Bischoff | A61B 3/107 606/4 |
| 2010/0331830 A1* | 12/2010 | Bischoff | A61F 9/008 606/5 |

FOREIGN PATENT DOCUMENTS

| | | | | |
|---|---|---|---|---|
| DE | 102007019813 A1 | 10/2008 | | |
| WO | WO 2012035403 A1 * | 3/2012 | | A01N 1/0226 |

* cited by examiner

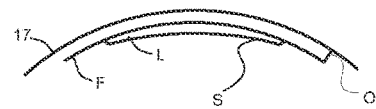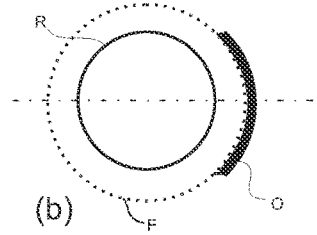
Fig. 6 (a) (b)
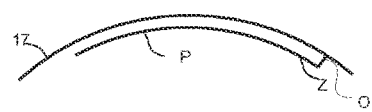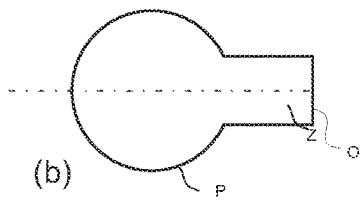
Fig. 7 (a) (b)
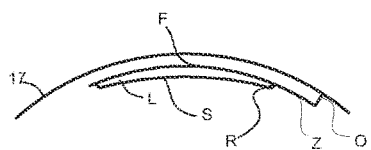
Fig. 8 (a)
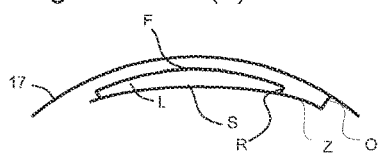
Fig. 9 (a)
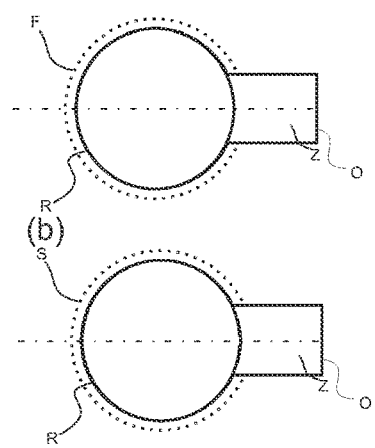
(b)
(b)
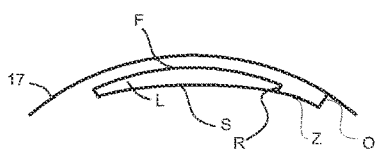
Fig. 10 (a)
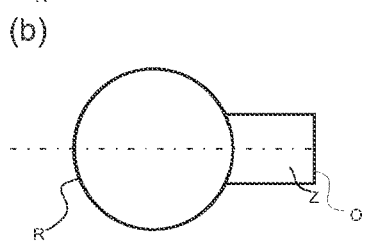
(b)
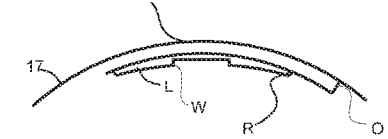
Fig. 11 (a)
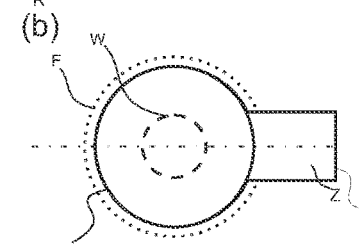
(b)
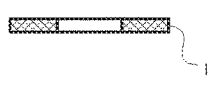
Fig. 12 (a)
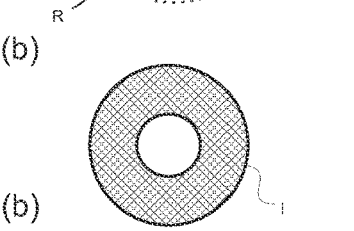
(b)
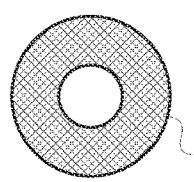
(b)

METHOD FOR EYE SURGERY

CROSS REFERENCE TO RELATED APPLICATIONS

This application claims priority from U.S. Provisional Patent Application No. 61/701,356, filed Sep. 14, 2012, and to the German Application No. 10 2012 018 420.4, filed Sep. 14, 2012, both of which are hereby incorporated by reference herein in its entirety.

FIELD

The invention relates to a planning unit for producing control data for a treatment device which produces at least one cutting surface in the cornea by means of a laser unit. The invention further relates to a treatment device which comprises a planning unit of the stated type.

The invention further relates to a method for producing control data for a treatment device which produces at least one cutting surface in the cornea by means of a laser unit.

Finally, the invention also relates to a method for eye surgery, at least one cutting surface being produced in the cornea by means of a treatment device comprising a laser unit.

BACKGROUND

In the prior art, a wide range of treatment methods having the purpose of refraction correction in the human eye are known. In this context, the purpose of the operation methods is to alter the cornea selectively so as to influence the light refraction in the eye. A plurality of operation methods are used for this purpose. At present, what is known as laser-assisted in situ keratomileusis, also known as LASIK for short, is the most widespread. In this context, a cornea lamella is initially detached from the cornea surface on one side and folded to the side. This lamella can be detached by means of a mechanical microkeratome, or also by means of what is known as a laser keratome, such as is marketed for example by Intralase Corp., Irvine, USA. After the lamella has been detached and folded to the side, the LASIK operation provides the use of an excimer laser, which removes, by ablation, the corneal tissue which is exposed under the lamella in this manner. After the volume present under the cornea surface has been vaporised in this manner, the cornea lamella is folded back onto the original spot again.

The use of a laser keratome to expose the lamella is advantageous compared to a mechanical blade, since the geometric precision is improved and the frequency of clinically significant complications is reduced. In particular, the lamella can be produced with a much more constant thickness if laser radiation is used. The cut edge is also precisely formed, and this reduces the risk of healing difficulties as a result of this boundary surface which remains even after the operation. However, a drawback of this method is that two different treatment devices have to be used, specifically on the one hand the laser keratome for exposing the lamella and on the other hand the laser which vaporises the corneal tissue.

These drawbacks are eliminated in a method which was implemented very recently by Carl Zeiss Meditec. In this lenticule extraction method, a cutting geometry which separates a cornea volume (known as a lenticule) in the cornea is formed in the cornea of the eye by means of a short-pulse laser, preferably a femtosecond laser. This is then removed manually by the operator. One advantage of this method is that the cutting quality is further improved by the use of the femtosecond laser.

Moreover, only one treatment device is now necessary; the excimer laser is no longer used.

A development of the method is referred to in the literature as the SMILE method, in which instead of producing a flap, merely a small opening cut provides access to the lenticule positioned under what is known as the cap. The separated lenticule is removed through this small opening cut, damaging the biomechanical integrity of the anterior cornea less than in LASIK, FLEX or PRK. In addition, fewer nerve fibres in the cornea are cut up in this manner, and this has a demonstrably favourable effect on the restoration of the original sensitivity of the cornea surface. The symptom of dry eyes, which often has to be treated after LASIK, is thus reduced in intensity and duration. Other complications following LASIK, which generally relate to the flap (for example folding, epithelial ingrowth in the flap bed), occur more rarely with no flap.

When producing cutting surfaces in the cornea by means of laser radiation, the optical radiation effect is usually exploited in that an optical aperture is produced by means of individual optical pulses, the duration of which may be between 100 fs and 100 ns. It is also known to introduce individual pulses, the energy of which is below a threshold for an optical aperture, into the tissue or material with an overlap, in such a way that material or tissue separation is achieved in this way too. This idea for producing a cut in the corneal tissue makes a large number of cuts possible.

It is also part of the prior art to increase the depth of field of a human eye in order to overcome the loss of accommodation of age-related farsightedness (presbyopia) (compensation for presbyopia). Another possibility consists in introducing an implant (also known as an inlay) into the cornea of at least one eye of an affected patient. In this case, the implant can be of an artificial nature, e.g. a ring or lens made of a plastics material (e.g. KAMRA®,)Flexivue®, or a correspondingly shaped implant made of a biomaterial or a transplant made of human corneal tissue.

It is also conventional for the currently available implants to produce a pocket-like cutting geometry in the cornea by means of a femtosecond laser keratome, which cutting geometry is determined for receiving the implant and simultaneously facilitates the introduction of the implant by the doctor.

In this case, it is helpful for the affected eye to have a far point in the range of between 0.3 m and infinity. If this is not the case, the refractive power of the eye must additionally be corrected by means of an optical aid (glasses or contact lenses). It is already possible to use surgical correction methods (PRK or LASIK using an excimer laser) to refractively correct affected eyes again before or after implanting an inlay (post-correction).

If the correction takes place after implanting an inlay, the interaction between the treatment method and the inlay poses a largely incalculable risk to the efficacy and safety of the method overall.

If the correction takes place before implanting an inlay, the conditions created by the previous refractive correction are not suitable for ensuring optimal implantation. In this case, there is therefore great potential for improving the efficacy and safety of the overall method of the compensation for presbyopia.

As lenticular extraction methods, the methods consolidated under the trade names ReLEx®, namely ReLEx® flex and ReLEx® smile of the company Carl Zeiss Meditec, are both fundamentally suitable for being combined with an implantation method in which, after the lenticule has been removed, an implant is placed in the cornea. The method ReLEx smile additionally makes it possible to use the pocket-like cutting geometry created as a result of the method to receive the implant and thereby offer a certain amount of mechanical stability. In any case, the known cutting geometry allows the inlay to substantially slip out of place after the operation, thereby disrupting the visual impression.

SUMMARY

In an embodiment, the present invention provides a planning unit produces control data for a treatment device for eye surgery which produces at least one cutting surface in a cornea of the eye using a laser unit. The planning unit includes a calculation module for establishing a cornea cutting surface. The calculation module is configured to establish the cornea cutting surface based on data of a refraction correction, to produce a control data set for actuating the laser unit for the cornea cutting surface, and to determine the cornea cutting surface in such a way that the cornea cutting surface contributes to fixing an implant in an interlocking manner.

BRIEF DESCRIPTION OF THE DRAWINGS

FIG. 6 is a schematic drawing of a lenticule geometry SMILE according to the prior art, FIG. 7 is a schematic drawing of a cutting geometry for a pocket according to the prior art, FIG. 8 is a schematic drawing of a first lenticule geometry according to the invention, FIG. 9 is a schematic drawing of a second lenticule geometry according to the invention, FIG. 10 is a schematic drawing of a third lenticule geometry according to the invention, FIG. 11 is a schematic drawing of a fourth lenticule geometry according to the invention, FIG. 12 is a schematic drawing of an inlay.

DETAILED DESCRIPTION

Figure 1:
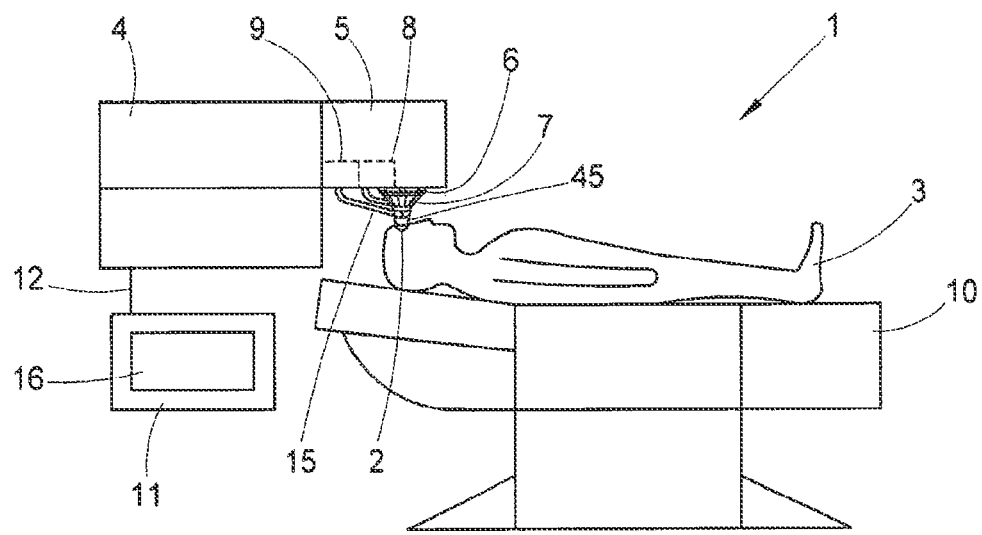
FIG. 1 is a schematic drawing of a treatment device comprising a planning unit for a secondary treatment in eye surgery refraction correction.

An aspect of the present invention is to provide a planning unit for producing control data, a treatment device for refraction correction eye surgery, and a method for producing control data for a treatment device of this type, in which optimal positioning of a cornea implant is ensured.

In an embodiment, the present invention provides a planning unit of the type mentioned at the outset which comprises calculation module for establishing a cornea cutting surface, the calculation module determining the new cornea cutting surface in such a way that it fixes the implant in an interlocking manner.

In an embodiment, the present invention also provides a treatment device which comprises a laser unit, which separates at least one cutting surface in the cornea by means of laser radiation in accordance with control data, and comprises a planning unit of the above-mentioned type for producing the control data, the planning unit determining the new cornea cutting surface in such a way that it fixes the implant in an interlocking manner.

In an embodiment, the present invention also provides a method for producing control data in accordance with the type stated at the outset, comprising: producing a control data set for the cornea cutting surface for actuating the laser unit, the planning unit determining the new cornea cutting surface in such a way that it fixes the implant in an interlocking manner.

In an embodiment, the present invention also provides a method comprising: producing a control data set for the cornea cutting surface, transferring the control data to the treatment device, and producing the cutting surfaces by actuating the laser unit using the control data set, the new cornea cutting surface being determined when producing the control data set in such a way that it fixes the implant in an interlocking manner.

The cap cut, i.e. the cut running substantially parallel to the cornea surface is selected in accordance with the invention so as to be substantially as large as the diameter of the lenticule. So that there is enough space when manually removing the lenticule, the cut can also be fractionally larger than the diameter of the lenticule. In addition, in accordance with the invention, an access cut is produced which connects the cap cut to another external opening cut, i.e. an opening cut arranged outside the optical zone of the eye. This access cut can preferably be strip shaped or in the shape of a segment of a circle.

This results in a cutting geometry which on the one hand produces a lenticule, but on the other hand keeps the resulting pocket as small as possible. In addition, the cutting geometry according to the invention comprises at least one access cut which is used to position the opening cut further outside the centre of the optical zone as far outside the optical zone as possible. By means of this tunnel-shaped opening cut, on the one hand, the lenticule can be removed, and on the other hand, after the lenticule has been removed, an implant can also be introduced. The smallness and the adapted geometry of the pocket result in a lack of room to move when decentring the implant. In addition, the tunnel-shaped opening cut helps to stabilise the implant in its position.

The access cut advantageously comprises two parallel edges, such that it is substantially rectangular and is generally situated at a depth of less than 300 μm. The lenticule cut and the cap cut are circular or oval shaped and have a diameter of approximately 4 to 8 mm. The cap thickness is less than 300 μm, preferably between 100 μm and 200 μm. The removal of the lenticule induces a change of refraction of between +10 dpt and −20 dpt, preferably of between +5 dpt and −10 dpt. Additional or exclusive cylinder correction and/or correction of other higher orders is possible. It is also possible to produce a lenticule with no refractive effect (0 dpt), but having a certain thickness (5 to 30 μm).

In this case, structures for improving the centring of the inlay are advantageous, for example round or oval-shaped recesses. These can optionally be included in the lenticule geometry. In particular, a corresponding structure can be produced by breaking up the lenticule profile in a diameter adapted to the implant.

A development of the invention results from a lenticule produced with a laser device (femtosecond, picosecond or nanosecond laser) being provided with additional cuts according to the invention even before it is manually removed from the cornea, which cuts are provided to prepare the lenticule for subsequent further use. In this case, this further use can be for example storage, use as a base material for tissue replacement material, as a substrate in the biotechnological production of tissue material, or as a transplant.

According to the invention, a lenticule to be extracted which is still in the eye of the "donor" is thereby pre-machined for subsequent further use. In the case of subsequent implantation of part of the removed tissue, cuts are advantageously produced in the lenticule which prepare or facilitate the marking and/or dissection of the lenticule into at least a part to be implanted (transplant) and the rest (waste) by a surgeon. Cuts are thus made, for example, for a transplant for correcting presbyopia having a diameter of approximately 3 mm inside a lenticule to be extracted having a diameter of approximately 7 mm. In another example according to the invention, in the volume of a lenticule provided for the extraction from the cornea of a myopic patient (extracted lenticule Lx), a lenticule provided for implantation in a hyperopic patient (implanted lenticule Li) having approximately the same diameter but a selectively altered shape with respect to Lx can be produced. In this way, the myopic defective vision of an eye of a patient can be corrected (e.g. sph=−8 dpt, cyl=0.5 dpt) and by means of the removed lenticule which has already been prepared in the eye of the first patient (the donor eye) or part of the lenticule which has been prepared therefor, hyperopic defective vision of an eye of another patient can be corrected (e.g. sph=3 dpt, cyl=1 dpt).

According to the invention, it is always the case that, from a geometric perspective, the lenticule Li is a partial volume of Lx.

The invention facilitates the improved use of tissue material accumulating during the course of a medical procedure on a patient by improving the possibilities for selective further use of the material.

It shall be understood that the features mentioned above and described in the following can be used not only in the specified combinations, but also in other combinations or in isolation, without departing from the scope of the present invention.

A treatment device for eye surgery is shown in FIG. 1 and provided with the general reference numeral 1. The treatment device 1 is formed for introducing laser cuts onto an eye 2 of a patient 3. For this purpose, the treatment device 1 comprises a laser unit 4, which emits, from a laser source 5, a laser beam 6 which is directed into the eye 2 or the cornea of the eye as a focused beam 7. Preferably, the laser beam 6 is a pulsed laser beam having a wavelength of between 300 nanometers and 10 micrometers. Further, the pulse length of the laser beam 6 is in the range of between 1 femtosecond and 100 nanoseconds, pulse repeat rates of 50 to 5000 kilohertz and pulse energies of between 0.01 microjoules and 0.01 millijoules being possible. The treatment device 1 thus produces a cutting surface in the cornea of the eye 2 by deflecting the pulsed laser radiation. A scanner 8 and a radiation intensity modulator 9 are therefore further provided in the laser unit 4 or the laser source 5 thereof for this purpose.

The patient 3 is positioned on a bed 10 which is adjustable in three spatial directions so as to orientate the eye 2 appropriately with respect to the incidence of the laser beam 6. In a preferred construction, the adjustment of the bed 10 can be motor-driven.

The actuation may take place in particular via a control apparatus 11, which basically controls the operation of the treatment device 1 and is connected to the treatment device via suitable data connections, for example connection lines 12, for this purpose. Naturally, this communication may also take place in other ways, for example by fibre optics or wirelessly. The control apparatus 11 carries out the corresponding settings and time control in the treatment device 1, in particular the laser device 4, and thus implements corresponding functions of the treatment device 1.

The treatment device 1 also further comprises a fixing means 15, which fixes the cornea of the eye 2 in position with respect to the laser unit 4. In this context, this fixing means 15 may comprise a known contact glass 45, against which the cornea is applied by negative pressure and which gives the cornea of the eye a desired geometric shape. Contact glasses of this type are known to a person skilled in the art from the prior art, for example from DE 102005040338 A1. The entire disclosure of this document, where it relates to the description of a construction of the contact glass 45 which is possible for the treatment device 1, is incorporated into the present document.

The treatment means 1 further comprises a camera (not shown here) which can take a picture of the cornea 17 of the eye through the contact glass 45. In this context, the illumination for the camera may be provided in both the visible and the infra-red light range.

The control apparatus 11 of the treatment device 1 also further comprises a planning unit 16, which will be explained in greater detail in the following.

Figure 2:
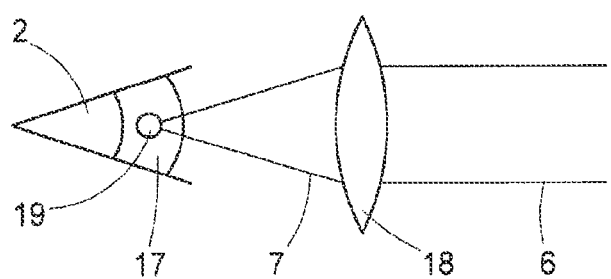
FIG. 2 is a schematic drawing of the effect of the laser radiation which is used in the treatment device of FIG. 1.

FIG. 2 shows schematically the operation of the incident laser beam 6. The laser beam 6 is focused and is incident on the cornea 17 of the eye 2 as the focused laser beam 7. Schematically illustrated optics 18 are provided for the focusing. In the cornea 17, they bring about a focus at which the laser radiation energy density is so high that, in combination with the pulse length of the pulsed laser radiation 6, a non-linear effect occurs in the cornea 17. For example, each pulse of the pulsed laser radiation 6 can produce at the focus 19 an optical aperture in the cornea 17 of the eye, which in turn initiates a plasma bubble (only shown schematically in FIG. 2). When the plasma bubble occurs, the tissue layer separation encloses an area greater than the focus 19, although the conditions for producing the optical aperture are only met at the focus 19. For an optical aperture to be produced by each laser pulse, the energy density, that is to say the fluence of the laser radiation, has to be above a particular threshold which is dependent on the pulse length. This relationship is known to a person skilled in the art for example from DE 69500997 T2. Alternatively, a tissue separation effect can also be achieved by way of pulsed laser radiation, in that a plurality of laser radiation pulses are emitted in a region where the focus spots overlap. A plurality of laser radiation pulses thus cooperate so as to achieve a tissue separation effect. However, the type of tissue separation used by the treatment device 1 is otherwise irrelevant to the following description; all that matters is that a cutting surface is produced in the cornea 17 of the eye 2.

In order to carry out an eye surgery refraction correction, a cornea volume is removed from the area inside the cornea 17 by means of the laser radiation 6, in that tissue layers are separated therein, which isolate the cornea volume and subsequently make it possible to remove it. For isolating the cornea volume which is to be removed, in the case of the laser radiation which is used in a pulsed manner, for example, the position of the focus 17 of the focused laser beam 7 in the cornea 17 is adjusted. This is shown schematically in FIG. 3. The refraction properties of the cornea 17 are selectively altered by removing the volume, so as to bring about the refraction correction. The volume is therefore generally lens-shaped, and is referred to as a lenticule.

Figure 3:
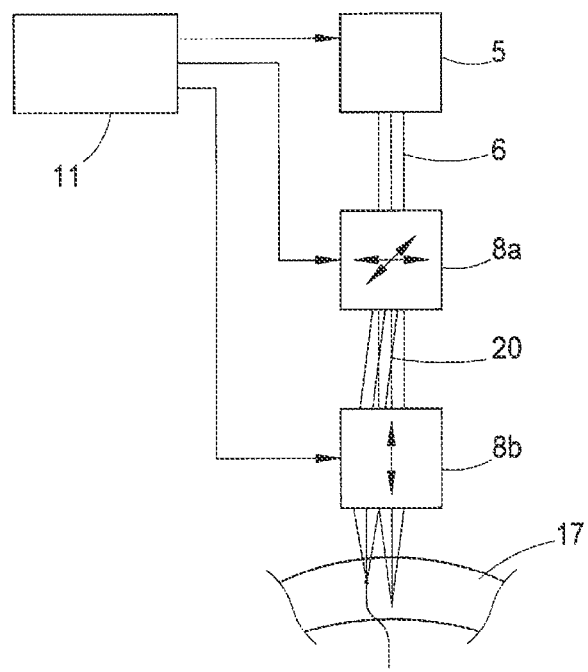
FIG. 3 is a further schematic drawing of the treatment apparatus of FIG. 1 relating to the introduction of the laser radiation.

In FIG. 3, the elements of the treatment device 1 are only included when they are necessary for understanding the cutting surface production. As stated above, the laser beam 6 is bundled at a focus 19 in the cornea 19, and the position of the focus 19 in the cornea is adjusted in such a way that energy focused at different points from laser radiation pulses is introduced into the tissue of the cornea 17 to produce the cutting surfaces. The laser radiation 6 is preferably provided by the laser source 5 as pulsed radiation. In the construction of FIG. 3, the scanner 8 is constructed in two parts, and consists of an xy scanner 8a, which in a variant is formed by two substantially orthogonally deflecting galvanometer mirrors. The scanner 8a deflects the laser beam 6 from the laser source 5 in two dimensions, in such a way that after the scanner 9 there is a deflected laser beam 20. The scanner 8a thus brings about an adjustment in the position of the focus 19 substantially perpendicular to the primary direction of incidence of the laser beam 6 in the cornea 17. To adjust the depth, a z scanner 8b is provided as well as the xy scanner 8a in the scanner 8, and is for example in the form of an adjustable telescope. The z scanner 8b ensures that the z position of the position of the focus 19, that is to say the position thereof on the optical axis of incidence, is altered. The z scanner 8b can be arranged upstream or downstream from the xy scanner 8a.

For the operating principle of the treatment device 1, it is irrelevant how the individual coordinates are allocated to the spatial directions, and also whether the scanner 8a deflects about mutually perpendicular axes. Rather, any scanner may be used which can adjust the focus 19 in a surface not containing the axis of incidence of the optical radiation. Further, any non-Cartesian coordinate system may also be used for deflecting or controlling the position of the focus 19. Examples of this are spherical coordinates and cylindrical coordinates.

The position of the focus 19 is controlled by means of the scanners 8a, 8b, actuated by the control apparatus 11, which applies corresponding settings to the laser source 5, the modulator 9 (not shown in FIG. 3) and the scanner 8. The control apparatus 11 ensures the suitable operation of the laser source 5 and the three-dimensional focus adjustment shown here by way of example in such a way that ultimately a cutting surface is formed which isolates a particular cornea volume which is to be removed for the refraction correction.

The control means 11 operates in accordance with predetermined control data which, for example in the laser unit 4 shown here merely by way of example, are predetermined as target points for the focus adjustment. The control data are generally combined into a control data set. This results in geometric specifications for the cutting surface to be formed, for example the coordinates of the target points, as a pattern. In this embodiment, the control data set thus also includes specific place values for the focus position adjustment mechanism, for example for the scanner 8.

Figure 4:
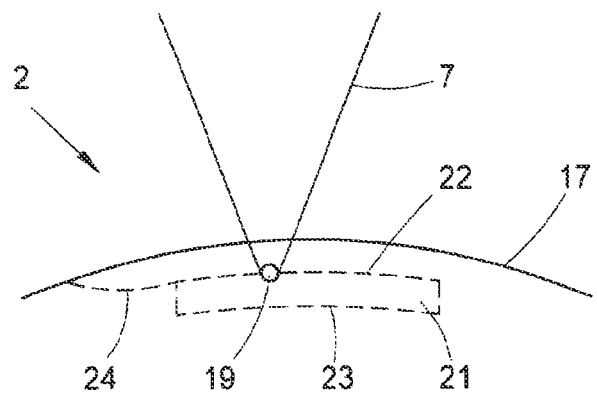
FIG. 4 is a schematic sectional view through the cornea of the eye to illustrate the removal of the volume of the cornea in connection with the eye surgery refraction correction.

The production of the cutting surface using the treatment device 1 is shown by way of example in FIG. 4. A cornea volume 21 in the cornea 17 is isolated by adjusting the focus 19 at which the focused beam 7 is bundled. For this purpose, cutting surfaces are formed, shown here by way of example as an anterior flap cutting surface 22 and a posterior lenticule cutting surface 23. In this context, these terms should be understood to be merely exemplary, and are intended to provide a reference to the conventional Lasik or Flex method for which the treatment device 1, as described above, is also configured. All that matters here is that the cutting surfaces 22 and 23 and edge cuts (not described further here), which bring the cutting surfaces 22 and 23 together at the edges thereof, isolate the cornea volume 21. Further, a cornea lamella which anteriorly defines the cornea volume 21 can be folded away by way of an opening cut 24, in such a way that the cornea volume 21 can be removed. In the preferred embodiment, this cornea lamella defined by the anterior cut has a constant thickness, but can also have a non-homogenous thickness, in particular a radius-dependent thickness.

Alternatively, the SMILE method may be used, in which the cornea volume 21 is removed by way of a small opening cut, as disclosed in DE 10 2007 019813 A1. The entire disclosure of this document is incorporated into the present document.

Figure 5:
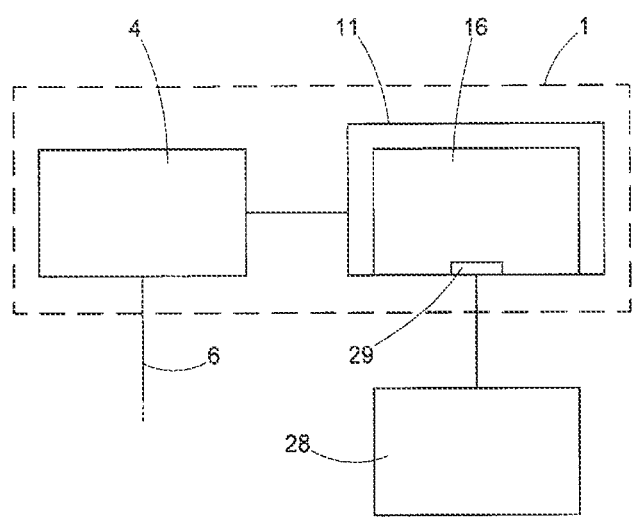
FIG. 5 is a schematic drawing relating to the construction of the treatment apparatus of FIG. 1, with particular emphasis on the planning unit provided therein.

FIG. 5 shows schematically the treatment device 1, and by way of this the significance of the planning unit 16 is to be described in greater detail. In this variant, the treatment device 1 comprises at least two means or modules. The previously described laser unit 4 emits the laser beam 6 onto the eye 2. In this context, the laser unit 4 is operated, as already shown, fully automatically by the control apparatus 11, that is to say upon a corresponding start signal the laser unit 4 starts to produce and deflect the laser beam 6 and thus produces cutting surfaces which are constructed in the above-described manner . The control signals required for the operation are received by the laser unit 5 of the control apparatus 11, to which corresponding control data have previously been provided. This takes place by means of the planning unit 16, which is shown in FIG. 5 merely by way of example as a component of the control apparatus 11. Naturally, the planning unit 16 may also be formed independently and communicate with the control means 11 in a wired or wireless manner. All that matters in this case is that a corresponding data transfer channel is provided between the planning unit 16 and the control apparatus 11.

The planning unit 16 produces a control data set, which is provided to the control apparatus 11 for carrying out the eye surgery refraction correction. In this context, the planning unit uses measurement data relating to the cornea of the eye. In the described embodiment , these data originate from a measuring unit 28, which has previously measured the eye 2 of the patient 2. Naturally, the measuring unit 28 may be configured, and convey the relevant data to the interface 29 of the planning unit 16, in any desired manner.

The planning unit now assists the operator of the treatment device 1 in establishing the cutting surface for isolating the cornea volume 21. This may go as far as fully automatically establishing the cutting surfaces, and this may take place for example in that the planning unit 16 determines from the measurement data the cornea volume 21 to be removed, the delimiting surfaces of which are defined as cutting surfaces, and produces corresponding control data for the control apparatus 11 therefrom. At the other end of the automation scale, the planning unit 16 may provide input options where a user inputs the cutting surfaces in the form of geometric parameters etc. Intermediate stages provide suggestions for the cutting surfaces, which are generated automatically by the planning unit 16 and can subsequently be modified by a user. In principle, all of the ideas explained previously in the more general part of the description above may be applied in the planning unit 16 in this context.

So as to carry out treatment, the planning unit 16 produces control data for the cutting surface production, which are subsequently used in the treatment device 1.

FIG. 6*a* is a schematic drawing of a cornea cross-section in the known SMILE method, illustrating the geometric relationships. The cornea 17 comprises an anterior cap cut F having an opening cut O. The posterior lenticule cut S isolated a lenticule volume L which can be removed through the opening cut O. Subsequently, an inlay can be introduced through the opening cut O.

FIG. 6*b* is a plan view of the cornea shown in FIG. 6*a*. In this context, the opening cut O has no stabilising effect on the inlay, which takes the place of the lenticule volume L.

FIG. 7*a* is a schematic drawing of a cutting geometry for a pocket according to the prior art in cross-section. The pocket cut P transitions into an access cut Z, which leads to an opening cut O. The inlay is introduced therethrough and thereby alters the geometry of the cornea 17. FIG. 7*b* is a plan view of the cornea shown in FIG. 7*a*.

The cutting geometries according to the invention are described in greater detail below.

FIG. 8*a* is a schematic drawing of a first cutting geometry in cross-section. The cap cut F transitions into an access cut Z, which leads to the opening cut O which is located outside the optical zone of the eye. The posterior lenticule cut S isolates a lenticule volume L, which is also limited by an edge cut R. FIG. 8*b* is a plan view of the cornea shown in FIG. 8*a*. The inlay is held reliably in the position thereof in particular by the edge cut R, which is intended to substantially correspond to the diameter of said inlay, although the cap cut F somewhat exceeds the diameter of the edge cut R in order to improve the removability of the lenticule L. However, the geometry of the access cut Z also contributes to the fixing of the inlay.

FIG. 9 is a schematic drawing of a further cutting geometry in cross-section. In this context, the lenticule cut S transitions into the access cut Z, which leads to the opening cut O. Edge cut R and cap cut F limit the lenticule.

FIG. 10 is a schematic drawing of a further cutting geometry in cross-section. In this context, the edge cut R ends precisely at the lenticule cut S; the inlay has no room to move and is fixed.

FIG. 11 is a schematic drawing of a further cutting geometry according to the invention in cross-section. In this context, the lenticule cut S comprises a step W, resulting in a protrusion A in the cornea 17, which additionally fixes an annular inlay. By means of this solution, the cap cut F can again be greater than the edge cut R in order to simplify the removal of the lenticule L, without the inlay being able to slip out of place.

FIG. 12 is a plan view of an annular inlay I of this type in cross-section but the inlay could also be spheric.

Figure 13:
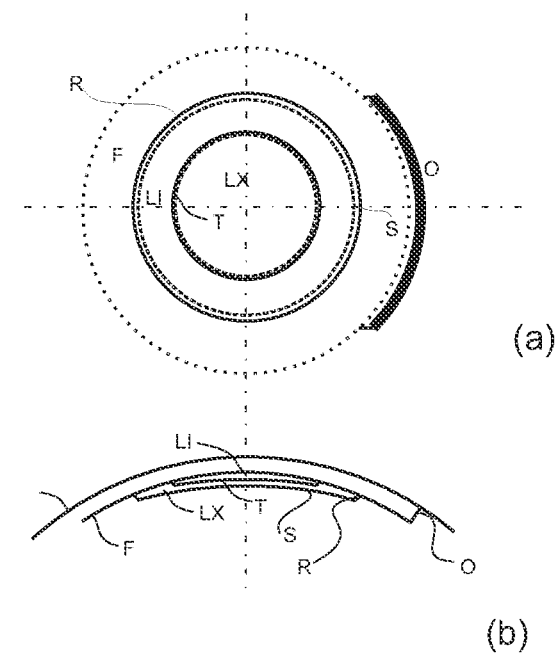
FIG. 13 is a schematic drawing of a fifth lenticule geometry according to the invention.
Figure 14:
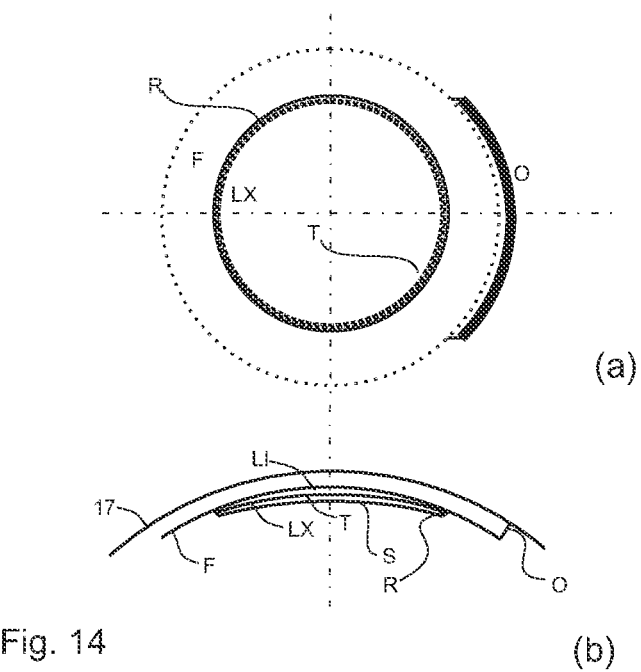
FIG. 14 is a schematic drawing of a sixth lenticule geometry according to the invention.

FIGS. 13 and 14 show cutting geometries according to the invention for obtaining cornea transplants having a desired refractive effect.

The lenticule L of the donor, which is calculated such that the refractive deficiency of the donor eye is corrected, is separated by a separating cut T into two parts such that one of the parts LI is suitable for bringing about the desired refractive correction in a recipient.

In FIG. 13, the relationships for a transplant for a hyperopy correction are shown, the part LI of the lenticule L provided for implantation has a diameter of approximately 3 mm when the diameter of the overall lenticule L is approximately 7 mm. The cuts F (cap cut), S (lenticule cut) and T (separating cut) are made in the eye of the patient before the lenticule is extracted through the opening cut O. After or during the extraction, the two lenticule parts LI and LX are separated and the part LI is classified and stored, or is directly implanted in a recipient.

In FIG. 14, as in FIG. 13, the relationships for a transplant are shown, which transplant is removed from a myopic patient and, with a lenticule part LI, delivers a transplant suitable for correcting hyperopy of another patient. For this purpose, the part LI provided for implantation has a diameter of approximately 7 mm, the separating cut T thus runs over the entire diameter of the lenticule cut S.

By means of the cutting geometries according to the invention, on the one hand, the centring of a cornea implant can be significantly improved, and on the other hand, implants of this type can be produced with greater precision and using available material.

In addition, it should further be noted that the treatment device 1 or the planning unit 16 naturally also specifically carries out the method explained generally in the above.

A further embodiment of the planning unit is in the form of a computer program or a corresponding data carrier comprising a computer program, which implements the planning unit on a corresponding computer, in such a way that the measurement data are inputted to the computer via suitable data transfer means and the control data are transferred from this computer to the control apparatus 11, for which purpose data transfer means known to a person skilled in the art may again be used.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A system for producing control data for controlling a laser so as to produce at least one cutting surface in a cornea of an eye of a patient, the system comprising:

a non-transitory computer readable medium having stored thereon instructions for:
  establishing a cornea cutting surface based on data of a refraction correction, and
  producing a control data set for actuating the laser to produce the cornea cutting surface,
wherein the cornea cutting surface is determined in such a way that it defines a lenticule,
wherein the lenticule has a geometry such that its removal from the eye of the patient will induce the refraction correction,
wherein the cornea cutting surface is also determined in such a way that it specifics cuts in the lenticule to be made prior to removal of the lenticule from the eye of the patient that facilitate dissection of the lenticule into at least (i) a transplant to be implanted into another eye of another patient and (ii) a waste component to be discarded,
wherein the transplant to be implanted into the another eye of the another patient is a partial volume of the lenticule, and
wherein the transplant has a geometry such that its implantation into the another eye of the another patient will induce a second refractive correction.

2. The system according to claim 1, further comprising: a laser system comprising the laser, wherein the laser is configured to produce the cutting surface in a cornea of the eye by laser radiation according to the control data.

3. The system according to claim 1, wherein the patient is a donor patient and the another patient is a recipient patient.

4. The system according to claim 3, wherein the cuts in the lenticule that facilitate the dissection of the lenticule into at least a part to be implanted into another eye of the recipient patient and a waste component include a separating cut that divides the lenticule into the transplant to be implanted into the another eye of the recipient patient and the waste component.

5. The system according to claim 4, wherein the separating cut defines, at least in part, the geometry of the transplant.

6. The system according to claim 1, wherein the cornea cutting surface defines a lenticule cut and a separating cut, wherein the lenticule cut isolates a lenticule volume having the geometry such that its removal from the eye of the patient will induce the refraction correction, wherein the separating cut separates the lenticule volume into the transplant to be implanted into the another eye of the another patient and a waste component.

7. The system according to claim 1, wherein the cornea cutting surface is further determined in such a way that it contributes to fixing an implant in the eye of the patient in an interlocking manner.

8. A method for producing control data for controlling a laser for eye surgery, the laser being configured to produce at least one cutting surface in a cornea of an eye of a patient, the method comprising:
  providing cornea data of the cornea of the eye of the patient;
  establishing a cornea cutting surface based on data of a refraction correction; and
  producing a control data set for actuating the laser to produce the cornea cutting surface,
  wherein the cornea cutting surface is determined in such a way that it defines a lenticule,
  wherein the lenticule has a geometry such that its removal from the eye of the patient will induce the refraction correction,
  wherein the cornea cutting surface is also determined in such a way that it specifies cuts in the lenticule to be made prior to removal of the lenticule from the eye of the patient that facilitate dissection of the lenticule into at least (i) a transplant to be implanted into another eye of another patient and (ii) a waste component to be discarded,
  wherein the transplant to be implanted into the another eye of the another patient is a partial volume of the lenticule, and
  wherein the transplant has a geometry such that its implantation into the another eye of the another patient will induce a second refractive correction.

9. The method according to claim 8, the method further comprising:
  transmitting the control data set to a laser system comprising the laser.

10. The method according to claim 8, wherein the cornea cutting surface is further determined in such a way that it contributes to fixing an implant in the eye of the patient in an interlocking manner.

11. A tangible non-transitory computer-readable medium having computer-executable instructions stored thereon, the computer-executable instructions comprising instructions for:
  providing cornea data of a cornea of an eye of a patient;
  establishing a cornea cutting surface based on data of a refraction correction; and
  producing a control data set for actuating a laser to produce the cornea cutting surface,
  wherein the cornea cutting surface is determined in such a way that it defines a lenticule,
  wherein the lenticule has a geometry such that its removal from the eye of the patient will induce the refraction correction,
  wherein the cornea cutting surface is also determined in such a way that it specifies cuts in the lenticule to be made prior to removal of the lenticule from the eye of the patient that facilitate dissection of the lenticule into at least (i) a transplant to be implanted into another eye of another patient and aka waste component to be discarded,
  wherein the transplant to be implanted into the another eye of the another patient is a partial volume of the lenticule, and
  wherein the transplant has a geometry such that its implantation into the another eye of the another patient will induce a second refractive correction.

12. The tangible non-transitory computer-readable medium of claim 11, the instructions further comprising instructions for transmitting the control data set to a laser system comprising the laser.

13. The tangible non-transitory computer readable medium according to claim 11, wherein the cornea cutting surface is further determined in such a way that it contributes to fixing an implant in the eye of the patient in an interlocking manner.

* * * * *